United States Patent [19]

Gradeff et al.

[11] Patent Number: 4,920,204

[45] Date of Patent: Apr. 24, 1990

[54] CERIC HYDROCARBYLOXY NITRATES AND THEIR USE IN ORGANIC SYNTHESIS

[75] Inventors: Peter S. Gradeff, Pottersville; Fred G. Schreiber, Highland Park, both of N.J.; Jean Grosbois, L'Isle Adam, France; Heiko Mauermann, New Brunswick, N.J.

[73] Assignee: Rhone-Poulenc Inc., New Brunswick, N.J.

[21] Appl. No.: 120,054

[22] Filed: Nov. 12, 1987

[51] Int. Cl.$^5$ ................................................ C07F 5/00
[52] U.S. Cl. ........................................................ 534/15
[58] Field of Search .......................................... 534/15

[56] References Cited

U.S. PATENT DOCUMENTS 4,489,000 12/1984 Gradeff et al. ........................ 534/15

OTHER PUBLICATIONS

Bradley et al., *J.C.S.* (1956), pp. 2260–2264.
Gradeff et al., *Inorg. Chem.*, 24 (1985), p. 1110.
Gradeff et al., *J. of the Less-Common Metals*, 126 (1986), pp. 335–338.

*Primary Examiner*—Brooks H. Hunt
*Assistant Examiner*—Virginia B. Caress

[57] ABSTRACT

Ceric hydrocarbyloxy nitrates having the general formula:

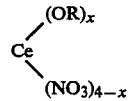

$x = 1, 2$ or $3$ are obtained by reaction of ceric ammonium nitrate with x moles of ammonia and an aliphatic, cycloaliphatic or aromatic alcohol having from two to twenty carbon atoms, and are useful in the preparation of ceric hydrocarbyl oxides difficult or expensive of access by other routes, and in synthesis of other organic ceric compounds.

13 Claims, No Drawings

CERIC HYDROCARBYLOXY NITRATES AND THEIR USE IN ORGANIC SYNTHESIS

Gradeff and Schreiber U.S. Pat. Nos. 4,489,000 and 4,663,439, patented Dec. 18, 1984 and May 5, 1987, respectively, provide a process for preparing ceric alkoxides which comprises reacting ceric ammonium nitrate with an alcohol, including a lower aliphatic alcohol, under anhydrous conditions in the presence of an anhydrous base at a temperature within the range from about $-30°$ C. to about 200° C., but preferably from 0° to about 150° C., until ceric alkoxide and the nitrate salt of the base are formed; ceric alkoxides of higher alcohols can be prepared by transetherification of the resulting ceric alkoxide with the higher alcohol, either simultaneously or sequentially, at a temperature within the range from about $-30°$ C. to about 200° C., thereby displacing the lower aliphatic alcohol and forming the ceric alkoxide of the higher alcohol, while distilling off free lower aliphatic alcohol in the course of the transetherification, to drive it towards completion; the nitrates formed during the reaction can be separated from the reaction mixture and the alkoxides isolated pure or as complexes with the alcohol, or in some cases the alkoxides can be used without separation from the reaction mixture in the presence of the nitrates.

The process is a considerable improvement over the method described by Bradley et al *J.C.S.* 1956 2260–64. Since cerium tetrachloride is unstable, the dipyridinium cerium hexachloride complex was Bradley et al's choice as starting material.

Cerium dioxide was first converted to ceric ammonium sulphate. Pure ceric hydroxide was precipitated from an aqueous solution of ceric ammonium sulphate and washed thoroughly. The freshly-prepared ceric hydroxide, suspended in absolute alcohol, was treated with anhydrous hydrogen chloride and then pyridine was added, which formed the insoluble dipyridinium cerium hexachloride complex $(Py)_2CeCl_6$. The complex was filtered, dried, and used for preparing the methoxide, ethoxide and isopropoxide directly, while the propyl, butyl, secondary butyl, neopentyl and n-pentyl alkoxides were made by alcohol interchange, i.e., transetherification, from the isopropoxide. The methoxide and ethoxide were also made by exchange from the isopropoxide.

The Gradeff et al patented process avoids the necessity described by Bradley et al of first preparing the ceric hydroxide from the ceric salt, in their case, ceric ammonium sulphate, and converting the hydroxide subsequently to the chloride, which needs to be stabilized as the pyridine complex. The process of the invention is direct and economical, and in addition utilizes ceric ammonium nitrate, a commercially available material that is relatively inexpensive.

Gradeff, Schreiber, Brooks and Sievers, *Inorganic Chemistry*, 24 (1985) 1110 reported that ceric ammonium nitrate (CAN) when dissolved in a low molecular weight alcohol such as methanol, ethanol, or isopropyl alcohol is reacted with an appropriate base, the ceric alkoxide is formed readily and quantitatively. It is necessary for CAN to be in solution prior to the addition of the base. Since higher alcohols are less solubilizing for CAN, they can be used in admixture with methanol. In this case, methoxide is probably formed first and solubilized in the form of a complex with the higher alcohol. The alcohol exchange takes place very easily at relatively low temperatures. In some cases, a solvent such as benzene, hexane, or toluene may be added to the reaction mixture to keep the alkoxide in solution and facilitate separation from sodium or ammonium nitrate. When anhydrous ammonia is used as a base, 4 mols is sufficient, as required by anhydrous reaction stoichiometry:

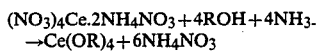

When an alkali alkoxide is used instead of ammonia, it is preferable to provide some excess (up to 2 equiv) over the required 4 equivalents.

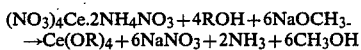

The excess of alkali alkoxide converts the $NH_4NO_3$ into alkali nitrate and ammonia, which makes the choice of workup less ambiguous and the material balance easier to establish.

Gradeff, Schreiber and Mauermann, *Journal of the Less-Common Metals* 126 (1986) 335–338 describe the preparation of ceric isopropoxide from ceric ammonium nitrate in dimethoxyethane (DME) and isopropanol (IPA). The preparation can be carried out quantitatively in a matter of a few hours and a procedure is described for doing so. However, the authors note that when ammonia is used instead of sodium isopropoxide, the reaction does not proceed to completion except with difficulty, because of an apparent equilibrium involving compounds having cerium-to-nitrate bonds of unknown structure. While the preparation of ceric isopropoxide in DME-IPA solution using sodium isopropoxide is quantitative, attempts to use ammonia as a base failed to provide a neat result.

In the absence of DME, the reaction with $NH_3$ in IPA is rapid and complete; mainly the separation of $NH_4NO_3$ from $Ce(OPr^i)_4$ presented difficulty. In the presence of DME the problem appeared to be at the reaction stage. It was thought at first that DME coordinatively affects the reactivity of the CAN but they did not find conclusive evidence for that. Since $Ce(OPr^i)_4$ exhibits considerable solubility in DME-IPA, the possibility of having a reversible reaction was examined and demonstrated in the following manner.

(a) When ceric isopropoxide in DME is stirred with $NH_4NO_3$ the color rapidly turns from bright yellow to orange with evolution of $NH_3$. Adding ammonia to that mixture changes the orange color to bright yellow again. A measured quantity of $Ce(OPr^i)_4$ and $NH_4NO_3$ in 1:7 mole ratio in DME was stirred for 3 hours at room temperature. Distillation at room temperature and analyses of the distillate via GC showed that 2 equivalents of IPA were liberated. The quantity of $NH_3$ was not measured.

(b) Cerium isopropoxide was reacted with 6 equivalents of $NH_4NO_3$. The supernatant was drawn off and dried. The IR spectrum in KBr (FIG. 1, Table 1) demonstrated the presence of cerium-to-nitrate bonds.

To the authors' knowledge, no other metal alkoxides have been made directly from nitrates which might explain the absence of information on exchange reactions in $M(OR)_n + NH_4NO_3$ systems.

Kinetic studies of this type of reaction involving $CE(OPr^i)_4$ are in progress and will be extended to other metal alkoxides, the authors stated.

In accordance with the present invention it has been determined that when this reaction is carried out in the presence of ammonia as a base, ceric hydrocarbyloxy nitrates are formed, having the formula:

$$\text{Ce} \begin{cases} (OR)_x \\ (NO_3)_{4-x} \end{cases} \quad x = 1, 2 \text{ or } 3 \qquad \text{I}$$

The reaction can be a single ceric hydrocarbyloxy nitrate, when x is 1, 2 or 3, or a mixture of any two, or all three, according to the proportions of the reactants. When a mixture is present, x can have a fractional value, representing the average x value according to the species present in the mixture, and their relative proportions.

The reaction is thought to proceed as follows:

1.
$$Ce(NO_3)_4 \cdot 2NH_3NO_3 + xNH_3 + yROH = Ce(OR)_{4-x}(NO_3)_x + (2+x)NH_4NO_3 + (y-x)ROH$$

y = at least x; x = 1, 2 or 3.

It is rather surprising that partial substitution of hydrocarbyloxy groups for nitrate groups produces a stable product that can be isolated as such. The ceric alkoxy nitrates are however quite stable, especially if substantially all ammonium nitrate is removed, thus inhibiting reversal of the above reaction.

In the above equation R is an aliphatic, cycloaliphatic or aromatic hydrocarbyl group having from two to about twenty carbon atoms, preferably alkyl, such as ethyl, propyl, isopropyl, butyl, isobutyl, sec-butyl, tert-butyl, amyl, isoamy, neopentanyl, hexyl, isohexyl, sec-hexyl, heptyl, isoheptyl, tert-heptyl, octyl, isooctyl, 2-ethyl hexyl, tert-octyl, nonyl, isononyl, tert-nonyl, decyl, neodecyl, isodecyl, sec-decyl, tert-decyl, dodecyl, hexadecyl, octadecyl, and eicosyl.

Exemplary cycloalkyl include cyclopropyl, cyclobutyl, cyclopentyl, cyclohexyl, cycloheptyl and cyclooctyl.

Exemplary aromatic hydrocarbyl include phenyl, phenethyl, phenbutyl, tolyl, xylyl, mesityl and naphthyl.

A mixture of ROH can be used, in which case the ceric hydrocarbyloxy nitrate can contain mixed hydrocarbyloxy groups, in the relative proportions of the ROH reactants.

The ceric hydrocarbyloxy nitrate may be in equilibrium among the various possible ceric hydrocarbyloxy nitrates, according to the following equation:

2.
$$(RO)_2Ce(NO_3)_2 \rightleftharpoons (RO)_3Ce(NO_3) + (RO)Ce(NO_3)_3$$

The relative proportion of the various ceric hydrocarbyloxy nitrate species will depend upon the nature of R and the solvent used.

The ceric hydrocarbyloxy nitrates, and particularly the ceric isopropoxy nitrates are of important practical utility in the preparation of ceric hydrocarbyl oxides, and particularly ceric isopropoxides, starting with ceric ammonium nitrate. Using the process of U.S. Pat. Nos. 4,489,000 and 4,663,439, Gradeff and Schreiber, patented Dec. 18, 1984 and May 5, 1987, respectively, the ceric hydrocarbyloxides and particularly the isopropoxides are obtained in accordance with the following reaction:

3.
$$Ce(NO_3)_6(NH_4)_2 + 6NaOR \rightarrow 6NaNO_3 + 2NH_3 + Ce(OR)_4 + 2ROH$$

The amount of anhydrous alkali metal hydrocarbyl oxide or alkoxide base is stoichiometric, since the function of the base alkali metal cation is to take up nitrate from the ceric ammonium nitrate starting material. An excess can be used but is not necessary, and in some cases is undesirable, as it might not be easy to separate from the ceric hydrocarbyl oxide (alkoxide).

It can be seen from the equation that there is no need for any additional alcohol. An excess of free alcohol however can be used.

As the reaction equation shows, 6 moles of sodium hydrocarbyl oxide (alkoxide) are required. Since this is an expensive reagent, this considerably increases the cost of the process. If, however, the starting material is ceric dihydrocarbyl oxide dinitrate, the corresponding ceric hydrocarbyl oxide can be formed according to the following equation:

$$\text{Ce} \begin{cases} RO \quad NO_3 \\ RO \quad NO_3 \end{cases} + 2NaOR \longrightarrow Ce(OR)_4 + 2NaNO_3 \qquad 4.$$

It is apparent from equation 4 that when ceric dialkoxy dinitrate is used, only two moles of the sodium alkoxide are required, instead of six, in reaction 3.

Thus, the ceric alkoxy nitrates provide a new and less expensive route to ceric alkoxides, starting from ceric ammonium nitrate, ammonia and aliphatic alcohol, in accordance with reaction equation 1, followed by reaction with NaOR according to reaction equation 4.

The reaction, in accordance with the invention, of ceric ammonium nitrate, ammonia and aliphatic, cycloaliphatic or aromatic alcohol proceeds with ease with any straight or branched chain aliphatic, cycloaliphatic or aromatic alcohol having from two to about ten carbon atoms.

The saturated aliphatic alcohols are preferred, for example, ethanol, propanol, isopropanol, butanol, isobutanol, sec-butanol, tert-butanol, pentanol, isopentanol, sec-pentanol, neopentanol, tert-pentanol, hexanol, heptanol, isoheptanol, octanol, isooctanol, 2-ethylhexanol, sec-octanol, tert-octanol, nonanol, isononanol, neodecanol, decanol, dodecanol, tetradecanol, octadecanol and eicosyl alcohol. However, unsaturated alkenyl alcohols can also be used.

Cycloaliphatic alcohols that can be used include cyclopropanol, cyclobutanol, cyclopentanol, cyclohexanol, cycloheptanol and cyclooctanol.

Aromatic alcohols include benzyl alcohol, phenol, naphthol, naphthyl alcohol, α-phenyl ethanol, β-phenylethanol, β-phenyl butanol, and mesityl alcohol.

The alcohol when a liquid under the reaction conditions can also serve as a solvent, and therefore an excess can be used without disadvantage, any excess preferably being recovered following completion of the reaction and recycled for reuse. Other inert solvents in addition to the reactant alcohol can also be used, such as benzene, hexane and acetonitrile. Also useful are glycol ethers, such as 1,2-dimethoxy ethane, 1,2-dimethoxy propane, 1,3-dimethoxy propane and tetrahydrofuran.

Any solvent present can easily be separated from the reaction product by distillation at atmospheric or reduced pressure, following completion of the reaction.

The reaction proceeds, desirably and preferably under anhydrous conditions, although small amounts of water can be tolerated, at a temperature within the range from about −30° C. to about 200° C., preferably from about 0° C. to about 150° C., most preferably at room temperature, depending on the solvent system used.

Anhydrous ammonia serves as the base, and is the only base that is employed in the process of the invention. Ammonia is used at least in an amount of x moles, sufficient to separate 2+x moles of ammonium nitrate from the reaction mixture, as per the stoichiometric proportions according to the reaction equation (1) above. By such separation, the reaction can be arrested at the ceric hydrocarbyloxy nitrate stage. An excess, i.e., more than 2+x moles ammonia, can be used, and may favor separation of ammonium nitrate, and facilitate isolation of cerium hydrocarbyloxy nitrate.

For example, to obtain cerium dialkoxy dinitrate, it is necessary to remove 4 moles of $NH_3NO_3$. The amount of ammonia necessary to achieve that cannot be explained on the basis of stoichiometry alone. In more practical terms the equation 1 can be written as follows:

$$Ce(NO_3)_y \cdot 2NH_3NO_3 + zNH_3 + yROH = Ce(NO_3)_{4-x}(OR)_x + (2+x)NH_4NO_3 + (y-x)ROH + (z-x)NH_3$$

x=<4>0; y=at least x; z=at least x but preferably higher.

In Example V, z=8. Theoretically, all 4 nitro groups should have reacted and the amount of $NH_3NO_3$ should have been 6. Instead, only 4.2 moles were formed which corresponds to a compound $Ce(NO_3)_{4-2.8}(OR)_{2.8}$. In the opinion of the inventors variations in operating conditions and characteristics of experiment would entail variations of the compound. It is indeed surprising that even using an excess of ammonia produced alkoxy nitrates, and not the expected tetra alkoxide as indicated in the prior art.

The reaction time is not critical. The reaction is continued until the desired hydrocarbyloxy nitrate product is formed. This may take from ten minutes to several hours, but it is not necessary to carry the reaction beyond a five hour reaction time. Usually, reaction is complete within from one-half to three hours.

The reaction can proceed quite rapidly at room temperature, and if it does, it very likely will also proceed at temperatures well below room temperature, down to −30° C., but there is usually no reason to incur the additional expense of cooling the reaction mixture. The upper limit on reaction temperature is imposed by the volatility of the reaction mixture or any component thereof, and their decomposition temperature, as well as side reactions involving ceric ammonium nitrate. At high temperatures, above 50° C., there is difficulty in keeping ammonia in the system. There is no reason to use a temperature above the boiling point of the reaction mixture at atmospheric pressure. The reaction temperature need not exceed 200° C., taking the above factors into consideration.

The amount of aliphatic, cycloaliphatic or aromatic alcohol is at least the stoichiometric amount y required to react with the ceric ammonium nitrate, but greater amounts can also be used. Larger than stoichiometric amounts will be used, of course, when the alcohol is also to function as a solvent, according to the dilution of the reaction mixture required.

The reaction mixture contains ammonium nitrate, and this can be separated from the hydrocarbyloxy nitrate during work-up. This salt is less soluble in the reaction mixture than the hydrocarbyloxy nitrate reaction product, and can be filtered off, and thereby separated from the reaction product. The reaction mixture can also be taken up in an inert solvent such as benzene, pentane or hexane, in which hydrocarbyloxy nitrate reaction product is soluble, and the ammonium nitrate insoluble, whereupon the ammonium nitrate is filtered off or centrifuged out.

Depending on reaction and work-up conditions, the hydrocarbyl nitrate can be isolated as associations with one or more molecules of alcohol or coordinated solvent.

For some applications the cerium hydrocarbyloxy nitrates can be used in the form in which they exist in the reaction mixture at the end of the reaction, without actually isolating them from the reaction mixture, or separating them from ammonium nitrate, which saves processing and handling costs.

For example, in the event that the ceric hydrocarbyloxy nitrate is being used as an intermediate in the preparation of a different ceric tetra-alkoxide, it is not necessary to isolate the ceric hydrocarbyloxy nitrate from the reaction mixture. All that is necessary is that the ammonium nitrate be separated by filtration. The sodium alkoxide of the desired ceric tetraalkoxide is then added to the reaction mixture and the reaction of the ceric hydrocarbyloxy nitrate to form the ceric tetra alkoxide then proceeds under the same conditions are described above, resulting in transetherification to form the desired product.

When the ceric hydrocarbyloxy nitrate is to be used as a starting material for the preparation of ceric tetra alkoxides, the process conditions are as described in Gradeff and Schreiber U.S. Pat. Nos. 4,489,000 and 4,663,439, substituting ceric hydrocarbyloxy nitrates for ceric ammonium nitrates, and of course reducing the amount of alkali metal alkoxide reagent. Accordingly, the disclosure thereof in No. 4,489,000, column 3, line 5 to column 4, line 51, and in No. 4,663,439, column 3, line 35 to column 4, line 60, is hereby incorporated by reference.

The following Examples in the opinion of the inventors represent preferred embodiments of the invention.

EXAMPLE I

Preparation of ceric diisopropoxy dinitrate 7 grams of ceric ammonium nitrate (equivalent to 0.01277 mole) was suspended in 20 ml (17 grams) of dimethoxyethane, and stirred for about five minutes. Addition of 1.8 grams (0.03 mole) isopropanol increased the solubility of the ceric complex with the dimethoxymethane. Then ammonia gas in an amount equivalent to 0.02554 mole was added to the mixture, causing the immediate formation of a white precipitate. Addition of the ammonia gas did not require longer than 30 seconds, because at the end of that time all of the ceric ammonium nitrate had dissolved and stirring became difficult because of the large amount of sodium nitrate precipitate. Thereafter, 20 ml of diethyl ether was added, and stirring was continued for 10 more minutes. The precipitate was then filtered off using a glass frit filter, and the clear dark red filtrate evaporated to dryness, yielding a dark red oil, ceric diisopropoxy dinitrate.

EXAMPLE II

Following the same procedure as in Example I, the compound ceric diisopropoxy dinitrate was prepared. To the solution of this complex containing 61.23 millimoles of cerium in 80 ml of isopropyl alcohol and 40 ml of dimethoxy ethane was added slowly 19.62 grams (122.46 millimole) sodium benzoate. The reaction mixture was filtered after standing for six days at room temperature, yielding a white precipitate and a red solution. The solution was dried, redissolved in dimethoxyethane, and pentane added to precipitate the compound, filtered, and the compound dried. NMR analysis of a purified sample indicated the formation of $Ce(O\text{-}isoC_3H_7)_2(O_2CC_6H_5)_2$. The crude compound was dissolved again in pentane, filtered, and set in dry ice. A yellow compound precipitated, 11.1 grams (30.8 millimoles) corresponding to a 50.23% yield.

EXAMPLES III TO V

One mole of ceric ammonium nitrate was dissolved in a mixture of 790 g dimethoxy ethane and 543 g isopropanol (a large excess) at room temperature. Ammonia was added in three molar ratios: 2, 4 and 8, causing immediate formation of ammonium nitrate as a white precipitate. The ammonium nitrate was filtered, dried and weighed.

| Example | Added $NH_3$ (Moles) | Recovered $NH_4NO_3$ (Moles) | Product |
|---|---|---|---|
| III | 2 | 2.6 | $Ce(NO_3)_{2.7}(OisoC_3H_7)_{1.3}$ |
| IV | 4 | 4 | $Ce(NO_3)_2(OisoC_3H_7)_2$ |
| V | 8 | 4.2 | $Ce(NO_3)_{1.2}(OisoC_3H_7)_{2.8}$ |

Under these conditions, using an excess of isopropanol, more than the theoretical amount of $NH_3$ (Example IV) was needed to get the desired ceric diisopropoxy dinitrate which corresponds to the formation of 4 moles of $NH_4NO_3$. Doubling the amount of $NH_3$ shifted the equilibrium of the reaction to the right only slightly, Example V, which shows that the desired product is the preferred one even if x is higher than theory. This allows for carrying out the process with ease.

An aliquot of the ceric diisopropoxy nitrate obtained in Example IV, as contained in the reaction mixture after filtering off, the ammonium nitrate, was reacted with 2 mole equivalents of Na-isopropoxide. Two moles of $NH_4NO_3$ were filtered from the reaction mixture, which contained ceric tetraisopropoxide.

Having regard to the foregoing disclosure, the following is claimed as the inventive and patentable embodiments thereof:

1. Ceric hydrocarbyloxy nitrates having the general formula:

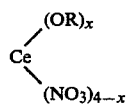

wherein x is 1, 2 or 3 and R is selected from the group consisting of aliphatic, cycloaliphatic and aromatic hydrocarbyl groups having from two to about twenty carbon atoms.

2. Ceric hydrocarbyloxy nitrates according to claim 1 in which R is alkyl.

3. A process for preparing ceric hydrocarbyloxy nitrates having the general formula:

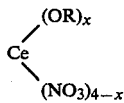

wherein x is 1, 2 or 3, and R is selected from the group consisting of aliphatic, cycloaliphatic and aromatic hydrocarbyl groups having from two to about twenty carbon atoms which comprises reacting ceric ammonium nitrate with an amount of ammonia within the range from at least 1 mole but less than 4 moles per mole of ceric ammonium nitrate and an aliphatic, cycloaliphatic or aromatic hydrocarbyl alcohol having from two to about ten carbon atoms at a temperature within the range from about $-30°$ C. to about 200° C. until ceric hydrocarbyloxy nitrate and ammonium nitrate are formed.

4. A process according to claim 3 in which an excess of at least 3 moles of ammonia but less than 4 moles per mole of ceric ammonium nitrate is used.

5. A process according to claim 3 in which the alcohol is present in an amount of at least 1 mole.

6. A process according to claim 3 in which R is alkyl.

7. A process according to claim 3, carried out in solution in an inert solvent.

8. A process according to claim 7 in which the solvent is the alcohol of which the hydrocarbyloxy nitrate is to be formed.

9. A process according to claim 3 carried out at a reaction temperature within the range from room temperature up to about 50° C.

10. A process according to claim 3 in which the cerium hydrocarbyloxy nitrate reaction product is recovered and separated from ammonium nitrate by filtration.

11. A process for preparing ceric alkoxides, which comprises reacting ceric ammonium nitrate and an alcohol with an amount of ammonia within the range from 1 mole but less than 4 moles per mole of ceric ammonium nitrate at a temperature within the range from about $-30°$ C. to about 200° C. until ceric alkoxy nitrate is formed, filtering off ammonium nitrate, and then reacting the ceric alkoxy nitrate with an alkali metal alkoxide of the alcohol of the desired ceric alkoxide at a temperature within the range from about $-30°$ C. to about 50° C. until reaction occurs to form the ceric alkoxide and the nitrate salt of the alkali metal.

12. A process according to claim 11 in which the alcohol present in the reaction mixture is the alcohol corresponding to the alkali metal alkoxide.

13. A process according to claim 11 in which the alcohol is an alcohol other than that corresponding to the alkali metal alkoxide.

* * * * *